United States Patent
Heidelbaugh et al.

(10) Patent No.: US 8,178,571 B2
(45) Date of Patent: May 15, 2012

(54) UNSUBSTITUTED AND SUBSTITUTED 4-BENZYL-1,3-DIHYDRO-IMIDAZOLE-2-THIONES ACTING AS SPECIFIC OR SELECTIVE ALPHA$_2$ ADRENERGIC AGONISTS AND METHODS FOR USING THE SAME

(75) Inventors: Todd M. Heidelbaugh, Fountain Valley, CA (US); Ken Chow, Newport Coast, CA (US); Phong X. Nguyen, Placentia, CA (US); Daniel W. Gil, Corona Del Mar, CA (US); John E. Donello, Dana Point, CA (US); Michael Garst, Newport Beach, CA (US); Larry A. Wheeler, Irvine, CA (US); John R. Cappiello, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/849,469

(22) Filed: Aug. 3, 2010

(65) Prior Publication Data

US 2010/0298395 A1    Nov. 25, 2010

Related U.S. Application Data

(62) Division of application No. 11/232,287, filed on Sep. 20, 2005, now Pat. No. 7,795,292.

(60) Provisional application No. 60/613,870, filed on Sep. 28, 2004.

(51) Int. Cl.
*A61K 31/4164* (2006.01)
*C07D 233/84* (2006.01)

(52) U.S. Cl. .................... 514/392; 548/316.4

(58) Field of Classification Search .................. 514/392; 548/316.4
See application file for complete search history.

(56) References Cited

U.S. PATENT DOCUMENTS

| | | | |
|---|---|---|---|
| 4,798,834 | A | 1/1989 | Merrit et al. |
| 4,798,843 | A | 1/1989 | Kruse |
| 6,124,300 | A | 9/2000 | Rajagopalos |
| 6,486,187 | B1 | 11/2002 | Venet |

FOREIGN PATENT DOCUMENTS

| | | |
|---|---|---|
| BR | 1499485 | 2/1979 |
| JP | 06067368 | 3/1994 |
| JP | 2002097312 | 1/2002 |
| JP | 2002097310 | 4/2002 |
| WO | WO 99/28200 | 6/1999 |
| WO | WO 01/00568 | 1/2001 |
| WO | WO 01/00586 | 1/2001 |
| WO | WO02/36162 | 5/2002 |
| WO | WO 03/099795 | 12/2003 |

OTHER PUBLICATIONS

Maeda et al. "Syntheses of 2-Mercapto-4-substituted Imidazole Derivatives with Antiinflammatory Properties" Chem. Pharm. Bull. 1984, vol. 32, pp. 2536-2543.*
Ruffolo, Jr., "a-Adrenoreceptors": Molecular Biology, Biochemistry and'. Pharmacology, (Progress in Basic and Clinical Pharmacology series, Karger, 1991).
Messier et ai, High Throughput Assays of Cloned Adrenergic, Muscarinic, Neurokinin, and Neurotiophin Receptors in Living Mammalian Cells, 1995, 76, pp. 308-311.
Conklin et ai, Substitution of three amino acids switches receptor specificity of Gqa to that of Glan; 1993, Nature 363: 274-6.
Dirig et ai, "Characterization of variables defining hindpaw withdrawal latency evoked by radiant thermal stimuli",J. Neurosci. Methods, 1997,76: 183-191.
J:Iargreaves et ai, "A new and sensitive method for measuring thermal nociception in cutaneous hyperalgesia", 1988, Pain 32: 77-88.
Dixon, W.J., "Efficient AnalysiS of Experimental Observations", Ann. Rev. Pharmacal. Toxico!., 1980,20: 441-462.
Minami et al, "Allodynia evoked by intrathecal administration of prostagland,in E2 to conscious mice", 1994,57 Pain, 217-223.

* cited by examiner

*Primary Examiner* — Joseph Kosack
(74) *Attorney, Agent, or Firm* — Doina G. Ene; John E. Wurst; Allergan, Inc.

(57) ABSTRACT

Compounds of Formula 1

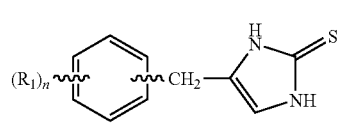

Formula 1 where the variables have the meaning defined in the specification are used to activate alpha$_2$ adrenergic receptors. The compounds of Formula 1 are incorporated in pharmaceutical compositions and are used as medicaments in mammals, including humans, for treatment of diseases and or alleviations of conditions which are responsive to treatment by agonists of alpha$_2$ adrenergic receptors.

7 Claims, No Drawings

UNSUBSTITUTED AND SUBSTITUTED 4-BENZYL-1,3-DIHYDRO-IMIDAZOLE-2-THIONES ACTING AS SPECIFIC OR SELECTIVE ALPHA$_2$ ADRENERGIC AGONISTS AND METHODS FOR USING THE SAME

CROSS-REFERENCE TO RELATED APPLICATION

This application is a Divisional of U.S. patent application Ser. No. 11/232,287, filed Sep. 20, 2005, which claims the benefit of U.S. provisional patent application Ser. No. 60/613,870, filed 28 Sep. 2004, each of which is incorporated herein by reference in its entirety.

FIELD OF THE INVENTION

The present invention relates to methods of using unsubstituted and substituted 4-benzyl-1,3-dihydro-imidazole-2-thiones as agonists of alpha 2 adrenergic receptors in mammals, and to certain novel compounds of the same general structure. The present invention also relates to pharmaceutical compositions containing one or more compounds having the unsubstituted and substituted 4-benzyl-1,3-dihydro-imidazole-2-thione structure as active ingredient for modulating the alpha$_2$ adrenergic receptors in mammals, and even more specifically for utilizing these compounds and pharmaceutical compositions to alleviate chronic pain, allodynia, muscle spasticity, diarrhea, neuropathic pain, visceral pain and other diseases and conditions.

BACKGROUND ART

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the α-adrenergic receptors, the reader's attention is directed to Robert R. Ruffolo, Jr., α-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting α-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

U.S. Pat. No. 4,798,843 describes (phenyl)-imidazole-2-thiones and substituted (phenyl)-imidazole-2-thiones which are used as dopamine B hydroxylase inhibitors.

PCT Publication WO 03/099795 published on Dec. 4, 2003 describes 4-(substituted cycloalkylmethyl) imidazole-2-thiones, 4-(substituted cycloalkenylmethyl) imidazole-2-thiones and related compounds and their use as specific or selective agonists of alpha$_{2B}$ and/or alpha$_{2C}$ adrenergic receptors.

PCT Publication WO 02/36162 published on May 10, 2002 discloses some cyloalkenyl-methyl-imidazoles, condensed cyclic-methyl imadazoles and an imidazole thione of the following structure

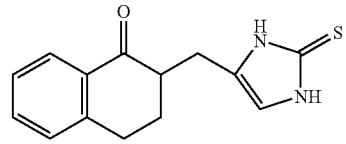

as an alpha$_{2B}$ or alpha$_{2C}$ selective agonist utilized for treatment of ocular neovascularization.

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2001 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. Pat. Nos. 6,545,182 and 6,313,172 describe phenylmethyl-(2-hydroxy)ethylthioureas which have no significant cardiovascular or sedative effects and are useful for alleviating chronic pain and allodynia. U.S. Pat. No. 6,534,542 describes cycloalkyl, cycloalkenyl, cycloalkylmethyl and cycloalkenylmethyl (2-hydroxy)ethylthioureas and their use as specific or selective agonists of alpha$_{2B}$ adrenergic receptors.

As further background to the present invention the compounds of U.S. Pat. Nos. 6,124,330 and 6,486,187 are mentioned. These compounds are said to have retinoic mimetic activity.

SUMMARY OF THE INVENTION

The present invention is directed to methods of activating alpha$_2$ adrenergic receptors in mammals using the compounds of Formula 1

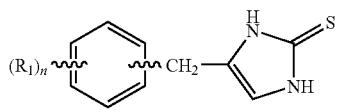

Formula 1 where n is an integer having the values of 0 to 5;
R$_1$ is independently selected from the group consisting of alkyl of 1 to 4 carbons, alkenyl of 2 to 4 carbons, alkynyl of 2 to 4 carbons, (CH$_2$)$_m$OR$_2$, (CH$_2$)$_m$NR$_3$R$_4$, (CH$_2$)$_m$CN, C(O)R$_5$, C(O)OR$_5$, (CH$_2$)$_m$SO$_2$R$_5$, aryl, heteroaryl, F, Cl, Br, I, fluoroalkyl containing 1 to 4 carbon atoms and 1 to 9 fluoro atoms, fluoroalkoxy containing 1 to 4 carbon atoms and 1 to 9 fluoro atoms, N$_3$ and NO$_2$, said heteroaryl having 1 to 3 heteroatoms independently selected from O, N and S, and said aryl and heteroaryl groups being optionally substituted with 1 to 3 radicals selected from the group consisting of alkyl of 1 to 4 carbons, alkenyl of 2 to 4 carbons, alkynyl of 2 to 4 carbons, (CH$_2$)$_m$OR$_2$, (CH$_2$)$_m$NR$_3$R$_4$, (CH$_2$)$_m$CN, C(O)R$_5$, C(O)OR$_5$, (CH$_2$)$_m$SO$_2$R$_5$, fluoroalkyl containing 1 to 4 carbon atoms and 1 to 9 fluoro atoms, fluoroalkoxy containing 1 to 4 carbon atoms and 1 to 9 fluoro atoms, N$_3$ and NO$_2$,
m is an integer having the values of 0, 1, 2, or 3;
R$_2$ is H, alkyl of 1 to 4 carbons, C(O)R$_5$, and aryl, or heteroaryl containing 1 to 3 heteroatoms independently selected from O, N and S, and said aryl and heteroaryl groups being optionally substituted with 1 to 3 radicals selected from the group consisting of alkyl of 1 to 4 carbons, alkenyl of 2 to 4 carbons, alkynyl of 2 to 4 carbons, (CH$_2$)$_m$OR$_2$, (CH$_2$)$_m$NR$_3$R$_4$, (CH$_2$)$_m$CN, C(O)R$_5$, C(O)OR$_5$, (CH$_2$)$_m$SO$_2$R$_5$, fluoroalkyl containing 1 to 4 carbon atoms and 1 to 9 fluoro atoms, fluoroalkoxy containing 1 to 4 carbon atoms and 1 to 9 fluoro atoms, N$_3$ and NO$_2$;
R$_3$ and R$_4$ are independently selected from the group consisting of H, alkyl of 1 to 4 carbons, C(O)R$_5$ and benzyl;
R$_5$ is independently H, alkyl of 1 to 4 carbons, aryl, or heteroaryl containing 1 to 3 heteroatoms independently selected from O, N and S, and said aryl and heteroaryl groups being optionally substituted with 1 to 3 radicals selected from the group consisting of alkyl of 1 to 4 carbons, alkenyl of 2 to 4 carbons, alkynyl of 2 to 4 carbons, (CH$_2$)$_m$OR$_2$, (CH$_2$)$_m$NR$_3$R$_4$, (CH$_2$)$_m$CN, C(O)R$_5$, C(O)OR$_5$, (CH$_2$)$_m$SO$_2$R$_5$, fluoroalkyl containing 1 to 4 carbon atoms and 1 to 9 fluoro atoms, fluoroalkoxy containing 1 to 4 carbon atoms and 1 to 9 fluoro atoms, N$_3$ and NO$_2$.

The present invention also includes novel compounds having the formulas

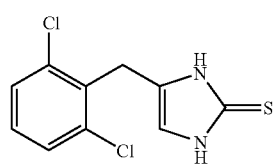

Compound 1

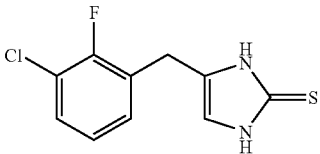

Compound 2

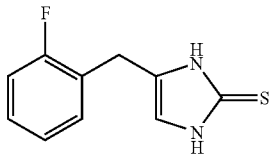

Compound 3

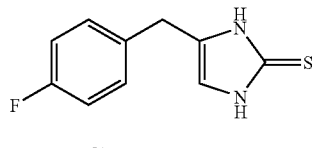

Compound 4

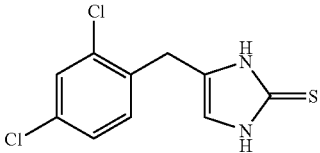

Compound 5

In another aspect the present invention is directed to pharmaceutical compositions containing as the active ingredient one or more compounds of Formula 1, and or one or more of the novel compounds shown above, the compositions being utilized as medicaments in mammals, including humans, for treatment of diseases and or alleviations of conditions which are responsive to treatment by agonists of alpha$_2$ adrenergic receptors. The compositions containing the compounds of the invention are primarily, but not exclusively, used for alleviation of chronic pain and/or allodynia. Some of the compounds used in the methods of the invention have the demonstrable advantageous property that they are specific or selective to alpha$_{2B}$ and/or alpha$_{2C}$ adrenergic receptors in preference over alpha$_{2A}$ adrenergic receptors, and some compounds have no or only minimal cardivascular and/or sedatory activity.

DETAILED DESCRIPTION OF THE INVENTION

A general description of the compounds used in the methods of the invention is provided in the Summary section of the present application for patent with reference to Formula 1. It will be readily apparent to those skilled in the art that some of the compounds depicted in Formula 1 may exist in trans (E) and cis (Z) isomeric forms. Moreover, some of the compounds of the invention may contain one or more asymmetric centers, such that the compounds may exist in enantiomeric as well as in diastereomeric forms. Unless it is specifically noted otherwise, the scope of the present invention includes all trans (E) and cis (Z) isomers, enantiomers, diastereomers and racemic mixtures. Some of the compounds of the invention may form salts with pharmaceutically acceptable acid or base, and methods using such pharmaceutically acceptable salts of the compounds of Formula 1 are also within the scope of the invention.

The imidazole-2-thione compounds of the present invention can undergo tautomeric transformations and can be depicted by the tautomeric formulas shown below. All tautomers of Formula 1 are within the scope of the invention.

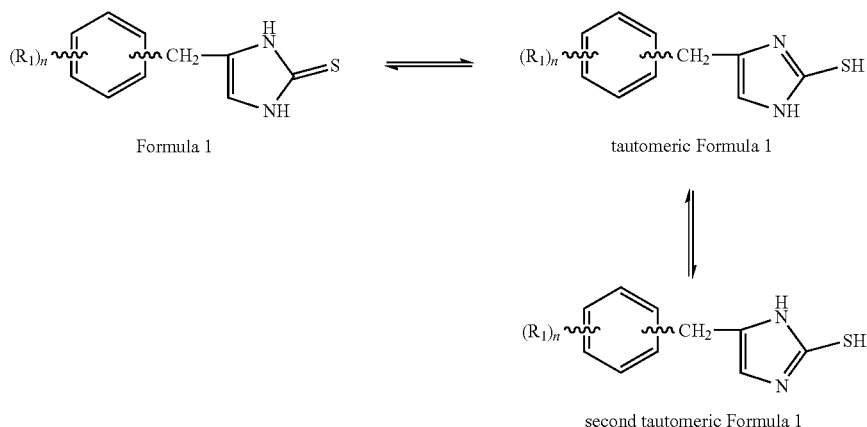

Formula 1 ⇌ tautomeric Formula 1 ⇌ second tautomeric Formula 1

Generally speaking and referring to Formula 1, in the compounds preferably used in the methods of treatment of the present invention The variable $R_1$ is preferably halogen, even more preferably F, Cl, Br, —$CH_3$, $CH_2CH_3$, —$CF_3$, —$CH_2OH$ preferably at the position(s) ortho and or meta to the bridge;

n is preferably 1 or 2;

m is preferably 1;

$R_2$ is preferably H;

$R_3$ and $R_4$ is preferably H or Me, and $R_5$ is preferably H, or Me.

The presently most preferred compounds used in the methods of treatment of the present invention are the novel compounds 1 to 5.

General Methods for Obtaining the Compounds of the Invention

Reaction Schemes A-B illustrate illustrate general methods for obtaining the 4-(benzyl-1,3-dihydro)-imidazole-2-thiones).

Reaction Scheme A employs an alpha-halo ketone of Formula 2 which can be obtained through commercial sources or prepared in accordance with known procedures in the chemical scientific and patent literature or by such modifications of known procedures which are readily apparent to the practicing synthetic organic chemist. The variables $R_1$ and n are defined as in connection with Formula 1. The compound of Formula 2 is reacted with formamide to provide the imidazole compounds of Formula 3. The imidazoles of Formula 3 are reacted with phenyl chlorothionoformate in the presence of sodium bicarbonate and water and subsequently treated with a base, such as triethylamine to produce 4-((benzyl-1,3-dihydro)-imidazole-2-thiones) of Formula 1.

Reaction Scheme A

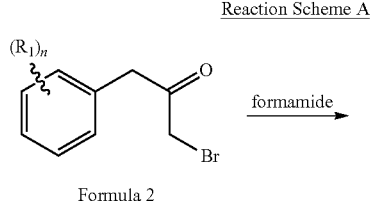

Formula 2

-continued

Formula 3

1) PhOC(S)Cl
   HOH, NaHCO₃
2) NEt₃

Formula 1

Reaction Scheme B employs an aldehyde starting material of Formula 4 which can be obtained through commercial sources or prepared in accordance with known procedures in the chemical scientific and patent literature or by such modifications of known procedures which are readily apparent to the practicing synthetic organic chemist. The aldehyde of Formula 4 is reacted with tosyl methylisocyanide (TosMIC) and sodium cyanide and thereafter heated in the presence of excess ammonia to produce the imidazole compounds of Formula 3. The imidazoles of Formula 3 are reacted with phenyl chlorothionoformate as described above to obtain compounds of Formula 1.

Reaction Scheme B

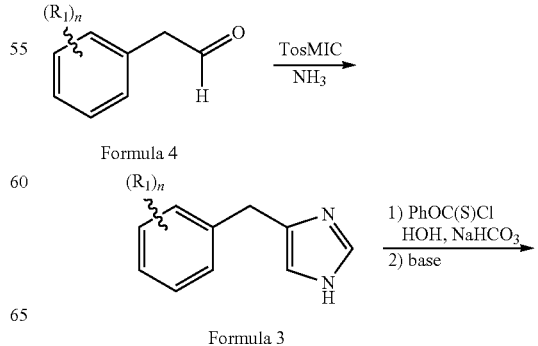

Formula 4

Formula 3

1) PhOC(S)Cl
   HOH, NaHCO₃
2) base

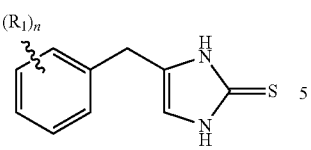

Formula 1

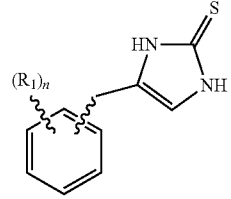

Formula 1

Reaction Scheme C provides a general method for preparing compounds of Formula 1. The variables in Reaction Scheme C are defined in the same manner as in connection with Formula 1. An aldehyde of Formula 5 is the starting material which can be obtained through commercial sources or prepared in accordance with known procedures in the chemical scientific and patent literature or by modifications of known procedures which are readily apparent to the practicing synthetic organic chemist. The aldehyde Formula 5 is reacted with a Grignard reagent of 4-iodo-1-triphenylmethyl-1H-imidazole to provide the triphenylmethyl (trityl) protected hydroxyimidazole compounds of Formula 6. Deoxygenation of the bridging hydroxyl moiety was accomplished by methods such as treatment with trifluoroacetic acid (TFA) in triethyl silane ($Et_3SiH$), followed by acidic deprotection of the trityl group to produce imidazoles of Formula 3. The imidazoles of Formula 3 are reacted with phenyl chlorothionoformate in the presence of sodium bicarbonate and water and subsequently treated with a base, such as triethylamine to produce 4-benzyl-1,3-dihydro-imidazole-2-thiones of Formula 1. The compounds of Formula 1 are within the scope of the present invention.

Reaction Scheme C

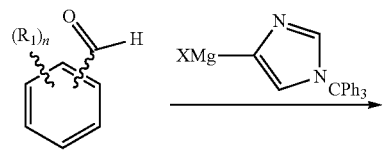

Formula 5

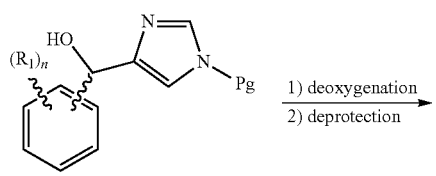

Formula 6
PG = protecting group

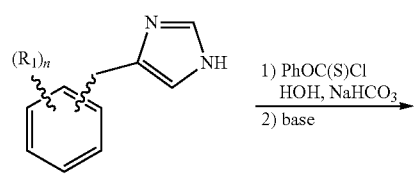

Formula 3

The synthesis of the novel compounds of the present invention is described in the Experimental section of the present application.

Biological Activity, Modes of Administration

The imidazole-2-thione compounds of Formula 1 and the novel compounds 1 through 5 are used in accordance with the present invention as agonists of alpha$_2$ adrenergic receptors. Some compounds of Formula 1 may act as specific or selective agonists of alpha$_{2B}$ and/or to alpha$_{2C}$ adrenergic receptors, in preference over alpha$_{2A}$ adrenergic receptors. The novel Compounds 3, 4 and 5 are specific agonists of alpha$_{2B}$ agonists in preference over alpha$_{2A}$ and alpha$_{2C}$ adrenergic receptors. The specific or selective activity of the compounds of Formula 1 in general and of the novel compounds of the invention can be tested in an assay titled Receptor Selection and Amplification technology (RSAT) assay, which is described in the publication by *Messier* et. Al., 1995, Pharmacol. Toxicol. 76, pp. 308-311 (incorporated herein by reference) and is also described below. Another reference pertinent to this assay is *Conklin* et al. (1993) Nature 363:274-6, Receptor Selection and Amplification Technology (RSAT) assay, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as beta-galactosidase, the activity of which can be easily measured in a 96-well format. Receptors that activate the G protein, $G_q$, elicit this response. Alpha$_2$ receptors, which normally couple to $G_i$, activate the RSAT response when coexpressed with a hybrid Gq protein that has a Gi receptor recognition domain, called Gq/i5.

NIH-3T3 cells are plated at a density of $2 \times 10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-beta-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, beta-galactosidase enzyme activity is determined by adding 200 μl of the chromogenic substrate (consisting of 3.5 mM o-nitrophenyl-beta-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the $alpha_{2A}$, $alpha_{2B}$ and $alpha_{2C}$ receptors.

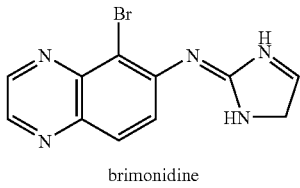

brimonidine

Results of the RSAT assay for the novel compounds of the invention are shown in Table 1 below.

| Biological Data : Intrinsic Activity | | | |
|---|---|---|---|
| Structure | Alpha 2A | Alpha 2B | Alpha 2C |
| Compound 1 | 0.74 | 1.11 | 1.18 |
| Compound 2 | 0.78 | 1.05 | NA |
| Compound 3 | NA | 1.3 | NA |
| Compound 4 | NA | 0.92 | NA |
| Compound 5 | NA | 0.95 | NA |
| Compound 6 | NA | 0.70 | 0.71 |

NA stands for "not active" at concentrations less than 10 micromolar.

Diseases that may be treated in accordance with this invention, generally speaking with compounds of Formula 1 and specifically with the novel compounds 1 through 5 include, but are not limited to neurodegenerative aspects of the following conditions:

MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy VASUCLAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

Generally speaking $alpha_2$ agonists, can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

$Alpha_2$ agonists including $alpha_{2B/2C}$ agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of $alpha_{2B}$ and/or $alpha_{2C}$ adrenergic receptors in preference over $alpha_{2A}$ receptors, if the compound is more active, preferably at least ten (10) times more active towards either $alpha_{2B}$ or towards $alpha_{2C}$ receptors than towards $alpha_{2A}$ receptors. It can be seen from these tables that many compounds of the invention are specific or selective agonists of $alpha_{2B}$ and/or $alpha_{2C}$ adrenergic receptors within the former definition, and in fact have no agonist like activity or only insignificant agonist-like activity on $alpha_{2A}$ receptors. Thus, the imidazole-2-thione compounds are used in accordance with the present invention for treating conditions and diseases which are responsive to treatment by $alpha_2$ including $alpha_{2B}$ and/or $alpha_{2C}$ adrenergic agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel disease (IBD), functional dyspepsia and ulcerative colitis. The activity of the $alpha_{2B/2C}$ specific or selective compounds of the invention is highly advantageous because the administration of these compounds to mammals does not result in sedation or in significant cardiovascular effects (such as changes in blood pressure or heart rate).

The compounds are used in accordance with the invention as highly effective analgesics, particularly in chronic pain models, with minimal undesirable side effects, such as sedation and cardiovascular depression, commonly seen with other agonists of the $alpha_2$ receptors.

In accordance with the invention the Compounds of Formula 1, including the novel compounds 1 through 5 may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula 1, including the novel compounds 1 through 5, and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used in an ophthalmic or infusion format, the formulation will usually contain one or more salts to influence the osmotic pressure of the formulation.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A∃ and A* fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

The following in vivo assays can be employed to demonstrate the biological activity of the compounds of the invention.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (i.e. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

Effects on Cardiovascular System

To test the effect of the compounds on the cardiovascular system, typically six cynomolgus monkeys are given 500 µg/kg of the test compound by intravenous injection (i.v.) Or 3 mg/kg by oral gavage. The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results of this test are expected to show that the compounds of the invention have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Typically four test animals per group are weighed (approximately 0.3 kg) and injected intraperitonealy (i.p.) with 1 ml/kg of the test compound formulated in approximately 10 to 50% dimethylsulfoxide (DMSO) vehicle. Animals typically receive a 0.1 mg/kg and a 1 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45-50 degrees centigrade to each rat hindpaw.

The results in this test are expected to show that the compounds of the invention do not provide analgesic effects in this bioassay of acute pain. *Alleviation of Chronic Pain*

A model in accordance with Kim and Chung 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra Xlll down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in d $H_2O$ and given in a volume of 1 ml/kg body weight using an 18-gauge, 3 inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. The post-drug threshold is compared to the pre-drug threshold and the percent reversal of tactile sensitivity is calculated based on a normal threshold of 15.1 grams.

The Mouse Sulprostone Model is an alternative model in which chronic pain, allodynia can be induced in mice through intrathecal treatment of the animals with 200 ng sulprostone (prostaglandin E2 receptor agonist) in 50% DMSO and in volume of Sul. In this model, the pain response to stroking the flank with a paint brush is scored 8 times over a 35 minute period starting 15 minutes following final administration of sulprostone. Minami et al., 57 Pain 217-223 (1994), hereby incorporated by reference. Sulprostone treatment alone elicits a score of 12-13 on a 16-point scale.

In variants of this model, allodynia can be induced using intraperitoneal injection of 300 μg/kg sulprostone or 30 μg/kg phenylephrine. Alternatively allodynia can be induced using intrathecal injection of 100 ng N-methyl-D-asparate (NMDA) or 30 ng phenylephrine (PE) formulated in $dH_2O$ in a volume of e.g. 5 microliters.

In either model, the compounds are formulated in $dH_2O$ and given in a volume of 1 ml/kg body weight for intraperitoneal (IP) dosing.

The results of these tests are expected to illustrate that the compounds of Formula 1, including the novel compounds 1 through 5 significantly alleviate allodynic pain, and based on these test and/or on the compounds ability to activate $alpha_{2B}$ and/or $alpha_{2C}$ adrenergic receptors in preference over $alpha_{2A}$ adrenergic receptors, the compounds of the invention are expected to be useful as analgesics without significant side effects.

Specific Embodiments, Experimental

Example A

Method A: Procedure for the preparation of 4-(2,6-dichloro-benzyl)-1,3-dihydro-imidazole-2-thione (Compound 1)

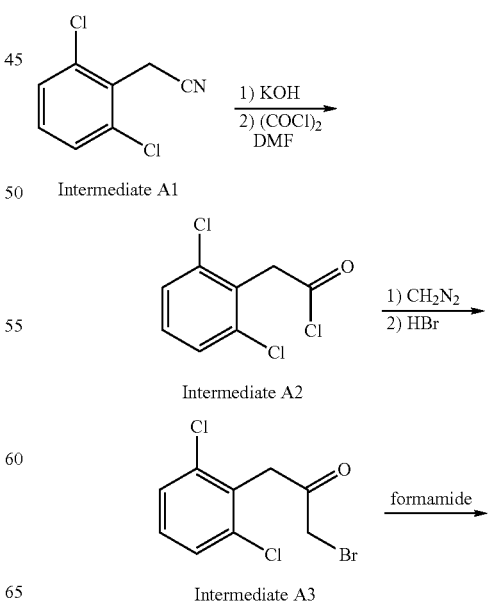

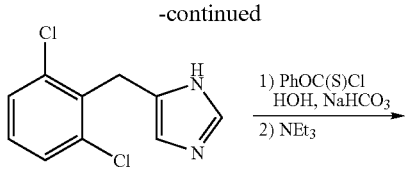

Intermediate A4

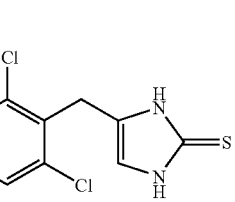

Compound 1

A solution of (2,6-dichloro-phenyl)-acetonitrile (Intermediate A1) (commercially available at Aldrich) (18.6 g, 100 mmol) in ethanol (40 mL) and water (50 mL) was treated with KOH (30 g) and the mixture was heated to 80° C. for 20 h. The mixture was quenched with HCl until pH 3. The product was extracted with chloroform (5×50 mL). The extracts were combined, dried over MgSO$_4$, filtered and evaporated to dryness. The product was (2,6-dichloro-phenyl)-acetic acid, 17 g (83%). A solution of (2,6-dichloro-phenyl)-acetic acid (10 g, 49 mmol) in benzene (200 mL) was treated with oxalyl chloride (32 mL, 2M in dichloromethane) followed by a few drops of dimethyl formamide. The mixture was allowed to stir for 3.5 h at rt. The solvent was removed under vacuum to give ~11.5 g of (2,6-dichloro-phenyl)-acetyl chloride (Intermediate A2).

The acid chloride, Intermediate A2 (6 g, 26 8 mmol) was added via pipette to a solution of diazomethane in ether (30 mmol) (generated from Diazald by standard Aldrich diazomethane kit) at 0° C. After 35 m, HBr (conc.) (10 mL) was added at 0° C. This was allowed to react for 35 m. The ether was removed and the mixture was neutralized with sodium bicarbonate solution. The organic layer was removed and dried over MgSO$_4$. The mixture was filtered and concentrated under reduced pressure to give 1-bromo-3-(2,6-dichloro-phenyl)-propan-2-one (Intermediate A3) (~5 g, 66%).

1-Bromo-3-(2,6-dichloro-phenyl)-propan-2-one (Intermediate A3) (~2.5 g) was heated in formamide for 2 h at 180° C. and 150° C. for 1 additional h. Water (50 mL) was added and the mixture was extracted with chloroform (4×50 mL). The solution was washed with brine (1×30 mL), dried over MgSO$_4$, filtered and evaporated to dryness. The residue was purified by chromatography on silica gel with 5% NH$_3$-MeOH: CH$_2$Cl$_2$ to give the product 5-(2,6-dichloro-benzyl)-1H-imidazole (Intermediate A4), 400 mg.

A solution of 5-(2,6-dichloro-benzyl)-1H-imidazole (Intermediate A4) (0.34 g, 1.5 mmol) in THF (6 mL) and water (6 mL) was treated with NaHCO$_3$ (1.2 g) at rt for 10 m. Phenyl chlorothionoformate (0.60 mL, ~4.3 mmol) was added and stirring was continued for 3 h. The mixture was diluted with water (10 mL) and extracted with ether (4×15 mL). The organic portions were combined, dried over MgSO$_4$, filtered and freed of solvent. The residue was dissolved in MeOH (6 mL) and treated with NEt$_3$ (0.6 mL) for 18 h. The solvent was removed under vacuum and the product was washed on a glass frit with CH$_2$Cl$_2$ to give a white solid 4-(2,6-dichloro-benzyl)-1,3-dihydro-imidazole-2-thione (Compound 1) in ~50% yield.

$^1$H NMR (300 MHz, DMSO-d$^6$): δ 12.0 (s, 1H), 11.7 (s, 1H), 7.50 (d, J=5.1 Hz, 2H), 7.35 (t, J=6.0 Hz, 1H), 6.04 (s, 1H), 3.98 (s, 2H).

Example B

Method B: Procedure for the preparation 4-(3-chloro-2-fluoro-benzyl)-1,3-dihydro-imidazole-2-thione (Compound 2)

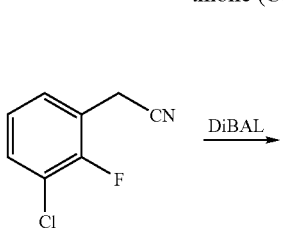

Intermediate B1

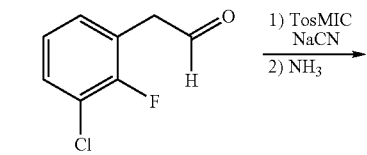

Intermediate B2

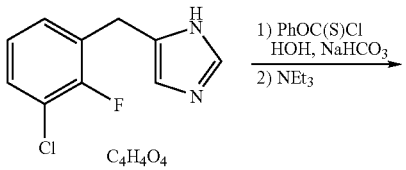

Intermediate B3

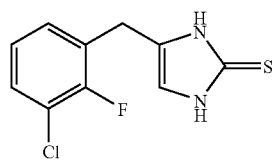

Compound 2

3-Chloro-2-fluorophenylacetonitrile (Intermediate B1) (commercially available from Matrix Scientific) (340 mg, 2 0 mmol) in ether (7 mL) and hexanes (7 mL) was cooled to 0° C. and treated with diisobutyl aluminum hydride (DIBAL, 3.0 mL, 3.0M in hexanes). After several minutes the mixture was diluted with 1 M HCl and stirring was continued for 15 m. The aqueous layer was separated and extracted with ether. The organic layers were dried over MgSO$_4$, filtered and evaporated to dryness. The residue, (3-chloro-2-fluoro-phenyl)-acetaldehyde (Intermediate B2) was employed in the next step without further purification.

The preparation of Intermediate B3 followed the procedure by Home et al. Heterocycles, 1994, 39, 139 incorporated herein by reference. A solution of (3-chloro-2-fluoro-phenyl)-acetaldehyde (Intermediate B2) (0.30 g, 4.57 mmol) in EtOH (7 mL) was treated with tosylmethyl isocyanide (TosMIC) (0.33 mg, 7.18 mmol) and NaCN (~10 mg, cat.). The resulting mixture was allowed to stir at rt for 20 minutes. The solvent was removed in vacuo and the residue was dissolved in ~7M NH$_3$ in MeOH (35 mL) and transferred to a re-sealable tube. This mixture was heated in a re-sealable tube at 90-100° C. for 12 h. Thereafter the mixture was concentrated and purified by chromatography on SiO$_2$ with 5%

MeOH (sat. w/NH₃):CH₂Cl₂ to give 5-(3-chloro-2-fluoro-benzyl)-1H-imidazole 0.4 g (31%) as an amber oil. The fumaric acid salt of the latter compound was formed in methanol and tetrahydrofuran. The solvent was removed and the salt was re-solvated in methanol:tetrahydrofuran and titurated with 20% ether-hexane. The solid was collected on a glass frit and dried under vacuum.

A solution of 5-(3-chloro-2-fluoro-benzyl)-1H-imidazole fumaric acid salt (Intermediate B3) (0.24 mmol) in THF (3 mL) and water (3 mL) was treated with NaHCO₃ (0.12 g) at rt for 10 m. Phenyl chlorothionoformate (0.11 mL, 0.6 mmol) was added and stirring was continued for 3 h. The mixture was diluted with water (10 mL) and extracted with ether (3×15 mL). The organic portions were combined, dried over MgSO₄, filtered and freed of solvent. The residue was dissolved in MeOH (5 mL) and treated with NEt₃ (0.3 mL) for 16 h. The solvent was removed under vacuum and the product was washed on a glass frit with CH₂Cl₂ to give a white solid, 4-(3-chloro-2-fluoro-benzyl)-1,3-dihydro-imidazole-2-thione (Compound 2).

¹H NMR (300 MHz, MeOD-d⁴): δ 7.38-7.34 (m, 1H), 7.16 (t, J=3.9 Hz, 1H), 7.11 (t, J=4.8 Hz, 1H) 6.53 (s, 1H), 3.87 (s, 2H).

Example C

Method C: Procedure for the preparation 4-(2-fluoro-benzyl)-1,3-dihydro-imidazole-2-thione (Compound 3)

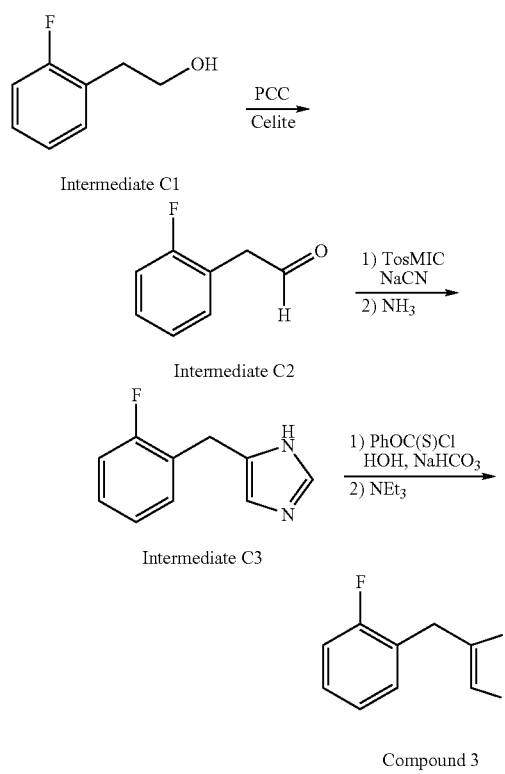

A mixture of 2-fluorophenethyl alcohol (Intermediate C1) (commercially available from Aldrich) (2.8 g, 20 mmol) in CH₂Cl₂ at −10° C. was oxidized by action of pyridinium chlorochromate: PCC (5 g, 23 mmol) in the presence of Celite (10 g) for 1 h at −10° C. and a couple hours at rt. The mixture was filtered through silica gel and the solvent was removed under vacuum to give (2-fluoro-phenyl)-acetaldehyde (Intermediate C2) 2.8 g (99%).

Use of (2-fluoro-phenyl)-acetaldehyde (Intermediate C2) in the appropriate process steps of Method B (note: the fumaric acid salts were not formed) gave a white solid 4-(2-fluoro-benzyl)-1,3-dihydro-imidazole-2-thione (Compound 3) 160 mg.

¹H NMR (500 MHz, DMSO-d⁶): δ 12.0 (s, 1H), 11.7 (s, 1H), 7.30-7.14 (m, 4H), 6.49 (s, 1H), 3.73 (s, 2H).

Example C-1

Use of (4-fluoro-phenyl)-acetaldehyde (commercially available from Aldrich) in the appropriate process steps of Method C gave a white solid 4-(4-fluoro-benzyl)-1,3-dihydro-imidazole-2-thione (Compound 4).

¹H NMR (300 MHz, DMSO-d⁶): δ 11.9 (s, 1H), 11.7 (s, 1H), 7.30-7.10 (m, 4H), 6.54 (s, 1H), 3.68 (s, 2H).

Example C-2

Use of 2-(2,4-dichloro-phenyl)-ethanol (commercially available from Aldrich) in Method C (where the Dess-Martin periodinane reagent, commercially available from Lancaster, was used in place of the PCC oxidant—procedure by Dess et al. *J. Am. Chem. Soc.* 1991, 113, 7277 incorporated herein by reference.) produced a white solid 4-(2,4-dichloro-benzyl)-1,3-dihydro-imidazole-2-thione (Compound 5).

¹H NMR (300 MHz, DMSO-d⁶): δ 12.0 (s, 1H), 11.8 (s, 1H), 7.59 (s, 1H), 7.40-7.30 (m, 2H), 6.47 (s, 1H), 3.77 (s, 2H).

Example D

Method D: Procedure for the preparation of 2'-(2-Thioxo-2,3-dihydro-1H-imidazol-4-ylmethyl)-biphenyl-4-carbonitrile (Compound 6)

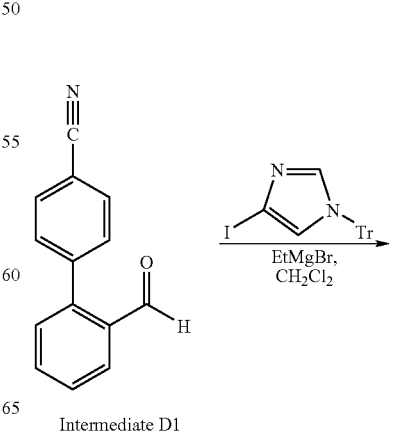

Intermediate D1

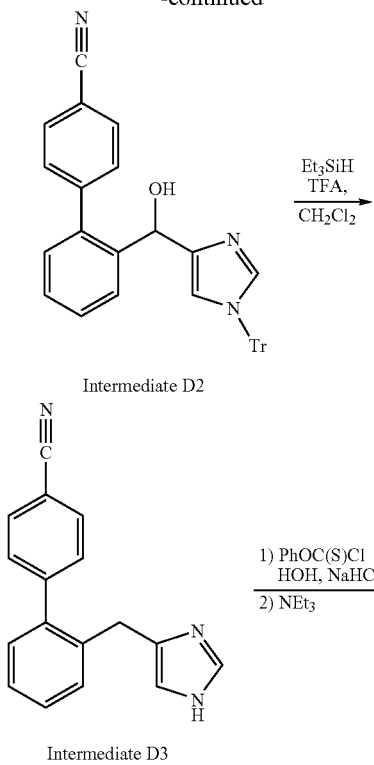

Intermediate D2

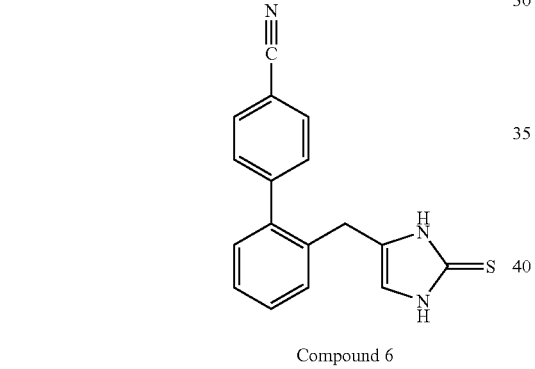

Intermediate D3

Compound 6

4-Iodo-1-trityl-1H-imidazole (2.5 g, 5.8 mmol) (commercially available from Synchem) in CH₂Cl₂ (35 mL) was cooled to 0° C. and treated with ethylmagnesium bromide (1.9 mL, 3.0M in ether). After several minutes the cooling bath was removed. The mixture was then stirred for an additional 1 h. A solution of 2'-formyl-biphenyl-4-carbonitrile (commercially available from Oakwood) (Intermediate D1) (1.0 g, 4.8 mmol) in CH₂Cl₂ (15 mL) was then added dropwise at 0° C. The flask was warmed to rt and stirred overnight. The mixture was quenched with H₂O (50 mL) and then treated with NH₄Cl (sat. aq) (50 mL). The product was extracted with CH₂Cl₂ (2×50 mL). The extracts were combined, dried over Na₂SO₄, filtered and concentrated to dryness. The residue was filtered through a pad of silica gel with 5% NH₃-MeOH: CH₂Cl₂ to give 2.5 g of 2'-[hydroxy-(1-trityl-1H-imidazol-4-yl)-methyl]-biphenyl-4-carbonitrile (Intermediate D2) as a white solid and used as such.

2'-[Hydroxy-(1-trityl-1H-imidazol-4-yl)-methyl]-biphenyl-4-carbonitrile (Intermediate D2) (2.4 g, 4.6 mmol) in CH₂Cl₂ (100 mL) was cooled to 0° C. and treated with triethyl silane, Et₃SiH (7.4 mL, 46 mmol) (commercially available from Aldrich) followed by trifluoroacetic acid, TFA (10.7 mL, 140 mmol) dropwise. After several minutes the cooling bath was removed and the mixture was stirred at rt for an additional 12 h. The reaction was quenched with solid NaHCO₃ followed by aqueous workup. The layers were separated and the organic layers were combined and dried over Na₂SO₄. The mixture was filtered and concentrated to dryness. The residue was purified by chromatography on silica gel with 3% NH₃-MeOH: CH₂Cl₂ to give the product 2'-(1H-imidazol-4-ylmethyl)-biphenyl-4-carbonitrile (Intermediate D3), 0.74 mg, 62% yield.

A solution of 2'-(1H-imidazol-4-ylmethyl)-biphenyl-4-carbonitrile (Intermediate D3) (0.36 g, 1.4 mmol) in THF (11 mL) and water (10 mL) was treated with NaHCO₃ (1.2 g) at rt for 5 m. Phenyl chlorothionoformate (0.95 mL, 7.0 mmol) was added and stirring was continued for 16 h. The mixture was diluted with water (10 mL) and extracted with ether (4×15 mL). The organic portions were combined, dried over MgSO₄, filtered and freed of solvent. The residue was dissolved in MeOH (15 mL) and treated with NEt₃ (2.0 mL) for 18 h. The solvent was removed under vacuum and the product was washed on a glass frit with CH₂Cl₂ and pentane to give a solid 2'-(2-thioxo-2,3-dihydro-1H-imidazol-4-ylmethyl)-biphenyl-4-carbonitrile (Compound 6) in 40% yield. ¹H NMR (300 MHz, DMSO-d⁶): δ 11.8 (s, 1H), 11.6 (s, 1H), 7.92 (d, J=9 Hz, 2H), 7.52 (d, J=9 Hz, 2H), 7.44-7.19 (m, 4H), 6.14 (s, 1H), 3.63 (s, 2H).

What is claimed is:

1. A method comprising administering to a mammal a pharmaceutical composition containing a therapeutically effective dose of a compound for the treatment of chronic pain, visceral pain, neuropathic pain, corneal pain; said compound having a structure selected from

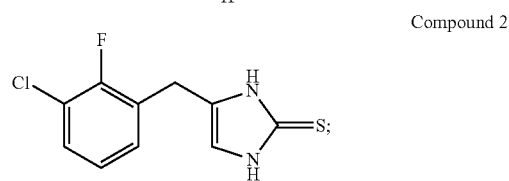

Compound 1

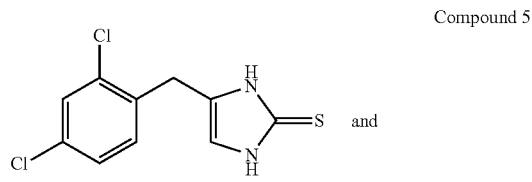

Compound 2

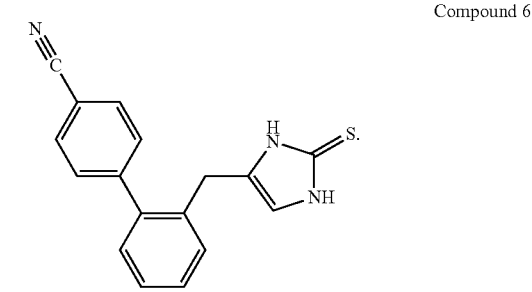

Compound 5 and

Compound 6

2. A method in accordance with claim 1 where the pharmaceutical composition is administered to the mammal to neuropathic pain.

3. A method in accordance with claim 1 where the pharmaceutical composition is administered to the mammal to visceral pain.

4. A method in accordance with claim 1 where the pharmaceutical composition is administered orally.

5. A method in accordance with claim 1 where the pharmaceutical composition is administered intraperitonially.

6. A method in accordance with claim 1 where the compound has the formula

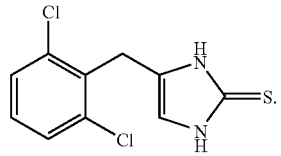

Compound 1

7. A method in accordance with claim 1 where the compound has the formula

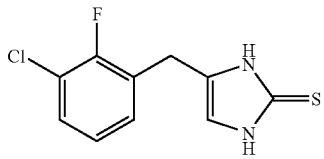

Compound 2

* * * * *